United States Patent [19]

Lombardino

[11] 4,434,163

[45] Feb. 28, 1984

[54] WATER-SOLUBLE BENZOTHIAZINE DIOXIDE SALTS

[75] Inventor: Joseph G. Lombardino, Niantic, Conn.

[73] Assignee: Pfizer Inc., New York, N.Y.

[21] Appl. No.: 367,066

[22] Filed: Apr. 13, 1982

Related U.S. Application Data

[63] Continuation-in-part of Ser. No. 268,980, Jun. 1, 1981, abandoned.

[51] Int. Cl.³ .................... C07D 401/12; A61K 31/54
[52] U.S. Cl. ........................................ 424/246; 544/49
[58] Field of Search ........................... 424/246; 544/49

[56] References Cited

U.S. PATENT DOCUMENTS

| | | | |
|---|---|---|---|
| 3,591,584 | 7/1971 | Lombardino | 260/243 |
| 4,116,964 | 9/1978 | Zinnes et al. | 544/49 |
| 4,233,299 | 11/1980 | Trummlitz et al. | 424/246 |
| 4,289,879 | 9/1981 | Lombardino | 544/49 |

FOREIGN PATENT DOCUMENTS 1544359  4/1979  United Kingdom .

OTHER PUBLICATIONS

J. G. Lombardino et al., "Potent Antiinflammatory N–Heterocyclic 3–Carboxamides of 4–Hydroxy-2-methyl-2H-1,2-benzothiazine 1,1–Dioxide", *Journal of Medicinal Chemistry*, vol. 16, No. 5, p. 493, (1973).

E. Nelson, "Solution Rate of Theophylline Salts and Effects from Oral Administration", *Journal of the American Pharmaceutical Association*, vol. 46, No. 10, p. 607, (1957).

A. E. Vivino, "Blood Theophylline Concentration Following the Oral Administration of Theophylline Ethylenediamine and Theophylline Isopropanolamine", *Journal of the American Pharmaceutical Association*, vol. 43, p. 234, (1954).

*Primary Examiner*—John M. Ford
*Attorney, Agent, or Firm*—Charles J. Knuth; Peter C. Richardson

[57] ABSTRACT

The water-soluble lysine and arginine salts of N-(2-pyridyl)-2-methyl-4-hydroxy-2H-1,2-benzothiazine-3-carboxamide 1,1-dioxide have been prepared. These novel salts are useful in therapy as non-steroidal antiarthritic agents, especially when administered by the parenteral route. Methods for preparing these salts from the corresponding acidic starting material and the appropriate amine base are provided.

5 Claims, No Drawings

WATER-SOLUBLE BENZOTHIAZINE DIOXIDE SALTS

CROSS REFERENCE TO RELATED APPLICATION

This application is a continuation-in-part of co-pending application Ser. No. 268,980, filed June 1, 1981 and now abandoned.

BACKGROUND OF THE INVENTION

This invention relates to new and useful benzothiazine dioxide salts. More particularly, it is concerned with certain novel water-soluble salts of N-(2-pyridyl)-2-methyl-4-hydroxy-2H-1,2-benzothiazine-3-carboxamide 1,1-dioxide, which are of especial value in view of their unique chemotherapeutic properties.

In the past, various attempts have been made to obtain new and better anti-inflammatory agents. For the most part, these efforts have involved the synthesis and testing of various steroidal compounds such as the corticosteroids or non-steroidal substances of an acidic nature such as phenylbutazone, indomethacin and the like, including a new agent known as piroxicam. The latter substance is a member of a class of anti-inflammatory 4-hydroxy-2H-1,2-benzothiazine-3-carboxamide 1,1-dioxides described and claimed in U.S. Pat. No. 3,591,584. However, in the continuing search for improved anti-inflammatory agents, there is a definite need for anti-arthritic agents that are adapted for parenteral administration.

SUMMARY OF THE INVENTION

In accordance with the present invention, it has now been found that certain novel water-soluble base salts of N-(2-pyridyl)-2-methyl-4-hydroxy-2H-1,2-benzothiazine-3-carboxamide 1,1-dioxide are useful as non-steroidal therapeutic agents for alleviating painful inflammatory conditions such as those caused by rheumatoid arthritis, for example. The novel salts of this invention are selected from the group consisting of the lysine and arginine salts of N-(2-pyridyl)-2-methyl-4-hydroxy-2H-1,2-benzothiazine-3-carboxamide 1,1-dioxide, which is an acidic compound of the formula:

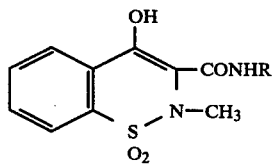

wherein R is 2-pyridyl. These salts are useful in alleviating the aforementioned arthritic effects, especially when given by the parenteral route of administration.

DETAILED DESCRIPTION OF THE INVENTION

In accordance with the process employed for preparing the novel salts of this invention, N-(2-pyridyl)-2-methyl-4-hydroxy-2H-1,2-benzothiazine-3-carboxamide 1,1-dioxide is contacted with at least an equivalent amount in moles of an organic amine base selected from the group consisting of lysine and arginine. This reaction is normally carried out in a polar protic solvent like water or a lower alkanol such as methanol, ethanol or isopropanol, etc. In general, the reaction is conducted at a temperature that is in the range of from about 20° C. up to about 100° C. for a period of about one-half to about 30 minutes, although it is usually most convenient in practice to conduct the reaction at the reflux temperature of the solvent. Upon completion of the reaction, the desired salt product is easily isolated in a conventional manner, e.g., by first evaporating the solvent from the reaction mixture, followed by trituration of the resulting solid residue or crude concentrate product with a suitable solvent system such as ethyl acetate/chloroform, etc. Alternatively, it is also possible to avoid the need for isolation by employing aqueous solutions of the salt as formed in situ by appropriate adjustment in concentration of the solution.

The starting materials required for preparing the novel salts of this invention are all known compounds. For instance, N-(2-pyridyl)-2-methyl-4-hydroxy-2H-1,2-benzothiazine-3-carboxamide 1,1-dioxide (piroxicam) is described in U.S. Pat. No. 3,591,584 to J. G. Lombardino, as well as in the paper of J. G. Lombardino et al., appearing in the *Journal of Medicinal Chemistry*, Vol. 16, p. 493 (1973), including its overall synthesis from readily available organic materials. The amine bases employed to prepare the novel amine addition salts of this invention are all commercially available materials.

The N-(2-pyridyl)-2-methyl-4-hydroxy-2H-1,2-benzothiazine-3-carboxamide 1,1-dioxide salts of the present invention are readily adapted to therapeutic use as anti-arthritic agents. For instance, the lysine and arginine salts of N-(2-pyridyl)-2-methyl-4-hydroxy-2H-1,2-benzothiazine-3-carboxamide, 1,1-dioxide exhibit anti-inflammatory activity in the standard carrageenin-induced rat foot edema test [described by C. A. Winter et al., *Proc. Soc. Exp. Biol. Med.*, Vol. 111, p. 544 (1962)]. The herein described benzothiazine dioxide salts exhibit additional advantages. For instance, even though N-(2-pyridyl)-2-methyl-4-hydroxy-2H-1,2-benzothiazine-3-carboxamide 1,1-dioxide (piroxicam) per se is very poorly water-soluble, the lysine and arginine salts of N-(2-pyridyl)-2-methyl-4-hydroxy-2H-1,2-benzothiazine-3-carboxamide 1,1-dioxide are readily flask soluble (i.e., instantaneously soluble) in said solvent and therefore are more rapidly absorbed into the blood stream upon oral administration than the corresponding less soluble calcium salt or even the anhydrous sodium salt of said particular drug (both of which are prepared according to the procedure already set forth in U.S. Pat. No. 3,591,584). Additionally, these particular salts afford water-clear, stable aqueous solutions even at very high concentration levels (>50 mg./ml.). This is a truly surprising fact when one considers that the tromethamine salt of N-(2-pyridyl)-2-methyl-4-hydroxy-2H-1,2-benzothiazine-3-carboxamide 1,1-dioxide and the corresponding triethanolamine salt are both poorly water-soluble and that the simple ammonium salt is found to be highly unstable when subjected to drying conditions under vacuum.

The herein described salts can be administered as anti-arthritic agents via either the oral, parenteral or topical routes. In general, these salts will be administered in doses ranging from about 5.0 mg. up to about 1000 mg. per day, although variations will necessarily occur depending upon the weight and condition of the subject being treated and the particular route of administration chosen. A dosage level that is in the range of from about 0.08 mg. to about 16 mg. per kg of body weight per day is usually preferred, although variations may occur depending upon the individual response to said medicament, as well as on the type of pharmaceutical formulation and the time intervals at which such administration is carried out. In some instances, dosage levels below the lower limit of the aforesaid range may be adequate, while in other cases higher levels may be employed, divided into several smaller doses for administration throughout the day.

The salts of this invention may be administered alone or in combination with pharmaceutically acceptable carriers by the various routes previously indicated, in a wide variety of dosage forms, i.e., they may be combined with various pharmaceutically acceptable inert carriers in the form of tablets, capsules, soft and hard lozenges, troches, hard candies, powders, sprays, creams, salves, suppositories, jellies, pastes, lotions, ointments, aqueous solutions and suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the salts of this invention are present in such dosage forms at concentration levels ranging from about 0.5% to about 90% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in hard geletin capsules; preferred materials also include lactose or milk sugar as well as high molecular weight polyethylene glycols. When aqueous solutions and suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of these amine salts in sesame or peanut oil or in aqueous propylene glycol or aqueous ethanol may be employed, as well as sterile aqueous solutions in distilled water. The aqueous solutions should be suitably buffered (pH>8) and the liquid diluent first rendered isotonic. These aqueous solutions are suitable for intravenous injection purposes. The oily solutions are suitable for intra-articular, intramuscular and subcutaneous injection purposes. Additionally, it is also possible to administer the aforesaid amine addition salts topically when treating inflammatory conditions of the skin or eye by way of creams, jellies, pastes, ointments, solutions and the like, in accordance with standard pharmaceutical practice.

The anti-inflammatory activity of the compounds of the present invention is demonstrated in the previously mentioned standard carrageenin-induced rat foot edema test. In this test, anti-inflammatory activity is determined as the percent inhibition of edema formation in the hind paw of male albino rats (weighing 150–190 g.) in response to a subplantar injection of carrageenin. The carrageenin is injected as a 1% aqueous suspension (0.05 ml.) one hour after oral administration of the drug, which is normally given in the form of an aqueous solution. Edema formation is then assessed by measuring the volume of the injected paw initially as well as three hours after the carrageenin injection. The increase in volume three hours after carrageenin injection constitutes the individual response. Compounds are considered active if the difference in response between the drug-treated animals (six rats/group) and a control group receiving the vehicle alone is significant on comparison with the results afforded by standard compounds like acetylsalicyclic acid at 100 mg./kg. or phenylbutazone at 33 mg./kg., both by the oral route of administration.

EXAMPLE 1

In a 1000 ml. Erlenmeyer reaction flask equipped with magnetic stirrer and reflux condenser, there were placed 3.5 g. (0.0105628 mole) of N-(2-pyridyl)-2-methyl-4-hydroxy-2H-1,2-benzothiazine-3-carboxamide 1,1-dioxide, 1.54 g. (0.0105628 mole) of L-lysine (available from the Aldrich Chemical Company, Inc., Milwaukee, Wis.) and 700 ml. of ethanol to form a yellow suspension. The latter suspension was then heated to reflux and treated with 10 ml. of water which was added slowly at the reflux point. The resulting yellow solution was then cooled to room temperature ($\sim$25° C.) and evaporated to near dryness while under reduced pressure to afford a yellow foam. The latter material was subsequently treated with 400 ml. of diethyl ether by slurrying overnight for a period of approximately 16 hours and then filtered in the usual manner to give a fine yellow solid. In this way, there were ultimately obtained 4.5 g. (89%) of the pure amorphous L-lysine salt of N-(2-pyridyl)-2-methyl-4-hydroxy-2H-1,2-benzothiazine-3-carboxamide 1,1-dioxide (as the hemihydrate with 0.25 mole of diethyl ether). The pure product was characterized by means of mass spectroscopy and infrared absorption spectra, in addition to elemental analysis.

Anal. Calcd. for $C_{15}H_{13}N_3O_4S.C_6H_{14}N_2O_2.0.5-H_2O.0.25\ C_2H_5OC_2H_5$: C, 52.31; H, 6.08; N, 13.86. Found: C, 52.52; H, 6.14; N, 13.77.

EXAMPLE 2

To a suspension of 5.0 g. (0.0151 mole) of N-(2-pyridyl)-2-methyl-4-hydroxy-2H-1,2-benzothiazine-3-carboxamide 1,1-dioxide in 400 ml. of water, there were added 2.77 g. (0.0159 mole) of L-(+)-arginine (available from Fisher Scientific Company, New York, N.Y.) and the resulting mixture was heated on a steam bath, with stirring, for a period of five minutes. The aqueous solution so obtained was then filtered to remove some minor insolubles, followed by concentration of the resulting filtrate in vacuo to yield a yellow oil as the residual liquid. Trituration of the latter material with a chloroform (80 ml.)/ethyl acetate (150 ml.) solvent system, followed by stirring at room temperature ($\sim$25° C.) overnight ($\sim$16 hours) under a dry nitrogen atmosphere then gave a yellow solid precipitate which was subsequently recovered by means of suction filtration. After drying the recovered solid material in vacuo at 57° C. (1.0 mm. Hg) to constant weight, there was ultimately obtained a 5.36 g. (70%) yield of the pure amorphous L-arginine salt of N-(2-pyridyl)-2-methyl-4-hydroxy-2H-1,2-benzothiazine-3-carboxamide 1,1-dioxide (as the hydrate), m.p. 142°–145° C. (decomp.). The pure product was further characterized by means of elemental analysis.

Anal. Calcd. for $C_{15}H_{13}N_3O_4S \cdot C_6H_{14}N_4O_2 \cdot H_2O$: C, 48.17; H, 5.58; N, 18.73. Found: C, 47.84; H, 5.72; N, 18.69.

EXAMPLE 3

An aqueous injectable solution is prepared by first intimately admixing one part by weight of the L-lysine salt of N-(2-pyridyl)-2-methyl-4-hydroxy-2H-1,2-benzothiazine-3-carboxamide 1,1-dioxide with 2.5 parts by weight of disodium phosphate with the aid of a mortar and pestle. The ground dry mixture so obtained is then sterilized with ethylene oxide and thereafter aseptically placed into vials and sealed. For purposes of intravenous administration, a sufficient amount of distilled water is added to each of the filled vials before use so as to ultimately provide a solution which contains 10 mg. of the active ingredient per each ml. of injectable solution.

I claim:

1. A water-soluble base salt of an acidic, anti-inflammatory 1,2-benzothiazine, said salt being a member selected from the group consisting of the lysine and arginine salts of N-(2-pyridyl)-2-methyl-4-hydroxy-2H-1,2-benzothiazine-3-carboxamide 1,1-dioxide.

2. A compound as claimed in claim 1 which is a lysine salt.

3. A compound as claimed in claim 1 which is an arginine salt.

4. A pharmaceutical composition comprising a pharmaceutically acceptable carrier and an effective anti-arthritic amount of a compound as claimed in claim 1.

5. A method for treating arthritic conditions in a warm-blooded animal, which comprises administering to said animal an effective anti-arthritic amount of a compound as claimed in claim 1.

* * * * *